(12) United States Patent
Foss et al.

(10) Patent No.: US 11,097,965 B2
(45) Date of Patent: Aug. 24, 2021

(54) MULTIPLE-BORE SOLUTE CARTRIDGE CARRIER

(71) Applicants: THE CLEVELAND CLINIC FOUNDATION, Cleveland, OH (US); PARKER HANNIFIN CORPORATION, Cleveland, OH (US)

(72) Inventors: Joseph Foss, Cleveland, OH (US); Paul Resendes, Cleveland, OH (US); Gino Banco, Cleveland, OH (US); Andrew Sylvester, Cleveland, OH (US)

(73) Assignees: THE CLEVELAND CLINIC FOUNDATION, Cleveland, OH (US); PARKER-HANNIFIN CORPORATION, Cleveland, OH (US)

( * ) Notice: Subject to any disclaimer, the term of this patent is extended or adjusted under 35 U.S.C. 154(b) by 385 days.

(21) Appl. No.: 15/556,126

(22) PCT Filed: Mar. 14, 2016

(86) PCT No.: PCT/US2016/022279
§ 371 (c)(1),
(2) Date: Sep. 6, 2017

(87) PCT Pub. No.: WO2016/149177
PCT Pub. Date: Sep. 22, 2016

(65) Prior Publication Data
US 2018/0044208 A1 Feb. 15, 2018

Related U.S. Application Data

(60) Provisional application No. 62/132,589, filed on Mar. 13, 2015, provisional application No. 62/132,618, filed on Mar. 13, 2015.

(51) Int. Cl.
*G01N 35/04* (2006.01)
*C02F 1/68* (2006.01)
(Continued)

(52) U.S. Cl.
CPC ............ *C02F 1/687* (2013.01); *A61G 12/001* (2013.01); *A61G 12/008* (2013.01);
(Continued)

(58) Field of Classification Search
CPC .................. G01N 2035/0443; G01N 35/1002
See application file for complete search history.

(56) References Cited

U.S. PATENT DOCUMENTS

| 3,876,234 A | 4/1975 | Harms |
| 4,022,205 A | 5/1977 | Tenczar |
| (Continued) | | |

FOREIGN PATENT DOCUMENTS

| EP | 2447697 A1 | 5/2012 |
| JP | S5980432 U | 9/1983 |
| (Continued) | | |

OTHER PUBLICATIONS

Korean Office Action for corresponding Korean Application Serial No. 2018-052816524, dated Aug. 3, 2018, pp. 1-10.
(Continued)

*Primary Examiner* — Jonathan M Hurst
(74) *Attorney, Agent, or Firm* — Tarolli, Sundheim, Covell & Tummino LLP

(57) ABSTRACT

A multiple-bore solute cartridge carrier 10) for use in a sterile fluid delivery system. The carrier includes a rotary housing (12) adapted for connection to the sterile fluid delivery system. The rotary housing has one or more bores (30) configured to receive a solute cartridge. The rotary housing, when connected to the sterile fluid delivery system, is selectively rotatable to facilitate creation of a desired sterile solution when sterile water from the fluid delivery system is flowed through the solute cartridge.

14 Claims, 7 Drawing Sheets

(51) Int. Cl.

| | | |
|---|---|---|
| *A61G 12/00* | (2006.01) | |
| *A61L 2/02* | (2006.01) | |
| *C02F 1/00* | (2006.01) | |
| *A61L 9/00* | (2006.01) | |
| *C02F 9/00* | (2006.01) | |
| *A61L 2/00* | (2006.01) | |
| *A61L 2/26* | (2006.01) | |
| *C02F 1/50* | (2006.01) | |
| *C02F 1/02* | (2006.01) | |
| *C02F 1/28* | (2006.01) | |
| *C02F 1/32* | (2006.01) | |
| *C02F 1/42* | (2006.01) | |
| *C02F 1/469* | (2006.01) | |
| *C02F 103/02* | (2006.01) | |
| *C02F 1/44* | (2006.01) | |
| *G01N 35/10* | (2006.01) | |
| *C02F 101/20* | (2006.01) | |

(52) U.S. Cl.
CPC ............ *A61L 2/0017* (2013.01); *A61L 2/022* (2013.01); *A61L 2/26* (2013.01); *A61L 9/00* (2013.01); *C02F 1/008* (2013.01); *C02F 1/50* (2013.01); *C02F 9/005* (2013.01); *A61L 2202/21* (2013.01); *C02F 1/001* (2013.01); *C02F 1/02* (2013.01); *C02F 1/283* (2013.01); *C02F 1/32* (2013.01); *C02F 1/42* (2013.01); *C02F 1/444* (2013.01); *C02F 1/4691* (2013.01); *C02F 1/68* (2013.01); *C02F 2001/427* (2013.01); *C02F 2101/20* (2013.01); *C02F 2103/026* (2013.01); *C02F 2201/006* (2013.01); *C02F 2201/008* (2013.01); *C02F 2209/006* (2013.01); *C02F 2209/02* (2013.01); *C02F 2209/03* (2013.01); *C02F 2209/05* (2013.01); *C02F 2209/06* (2013.01); *C02F 2209/40* (2013.01); *C02F 2301/043* (2013.01); *C02F 2303/04* (2013.01); *G01N 35/1002* (2013.01); *G01N 2035/0443* (2013.01)

(56) References Cited

U.S. PATENT DOCUMENTS

| | | | |
|---|---|---|---|
| 4,495,067 A | | 1/1985 | Klein et al. |
| 5,032,265 A | | 7/1991 | Jha et al. |
| 5,259,954 A | | 11/1993 | Taylor |
| 5,919,357 A | | 7/1999 | Wilkins et al. |
| 6,080,313 A | | 6/2000 | Kelada |
| 6,139,571 A | | 10/2000 | Fuller et al. |
| 6,164,314 A | | 12/2000 | Saputo et al. |
| 6,197,260 B1 | * | 3/2001 | Bradshaw ............ B01F 13/002 |
| | | | 210/295 |
| 6,302,864 B1 | | 10/2001 | Nowosielski |
| 6,325,968 B1 | * | 12/2001 | Fricker ................ A61L 2/18 |
| | | | 422/28 |
| 6,423,219 B1 | | 7/2002 | Chandler |
| 6,656,428 B1 | * | 12/2003 | Clark ................... B01L 3/502 |
| | | | 422/404 |
| 7,017,953 B2 | | 3/2006 | Benscoter et al. |
| 7,250,619 B2 | | 7/2007 | Taylor et al. |
| 2002/0162778 A1 | | 11/2002 | Peabody et al. |
| 2005/0171501 A1 | | 8/2005 | Kelly |
| 2006/0169719 A1 | | 8/2006 | Bui |
| 2007/0154976 A1 | * | 7/2007 | Taniguchi ............ G01N 33/723 |
| | | | 435/25 |
| 2008/0146991 A1 | | 6/2008 | Hernandez et al. |
| 2009/0182263 A1 | | 7/2009 | Ulichney et al. |
| 2009/0283409 A1 | | 11/2009 | Stern et al. |
| 2009/0321339 A1 | | 12/2009 | Suzuki et al. |
| 2010/0307973 A1 | | 12/2010 | Grcevic |
| 2011/0006790 A1 | | 1/2011 | Kirkaune |
| 2011/0196319 A1 | | 8/2011 | Arscott, II et al. |
| 2013/0224878 A1 | | 8/2013 | Wilson et al. |
| 2014/0021115 A1 | | 1/2014 | Ellegaard |
| 2014/0124430 A1 | | 5/2014 | Herges et al. |
| 2016/0144364 A1 | * | 5/2016 | Edwards ............. B01L 3/0203 |
| | | | 436/501 |

FOREIGN PATENT DOCUMENTS

| | | |
|---|---|---|
| JP | 2002500068 A | 1/2002 |
| JP | 2002538945 A | 11/2002 |
| JP | 2007501061 A | 1/2007 |
| JP | 2007521037 A | 8/2007 |
| JP | 2007252396 A | 10/2007 |
| JP | 2009028602 A | 2/2009 |
| JP | 5242787 B2 | 7/2013 |
| KR | 20030008504 A | 1/2003 |
| KR | 1012191 B1 | 2/2011 |
| WO | 2011/055133 A2 | 5/2011 |

OTHER PUBLICATIONS

Korean Office Action for corresponding Korean Application Serial No. 2018-052816670, dated Aug. 3, 2018, pp. 1-14.
International Search Report corresponding to International App. No. PCT/US2016/022287, dated Jul. 16, 2016, pp. 1-16.
European Office Action for the corresponding European Application Serial No. 16712611.9, dated Dec. 21, 2020, pp. 1-12.
Japanese Office Action for corresponding Japanese Application Serial No. JP2017-547454, dated Oct. 31, 2019, pp. 1-4.
European Examination Report for corresponding European Application Serial No. 16712609.3 dated Mar. 11, 2021, pp. 1-4.

* cited by examiner

MULTIPLE-BORE SOLUTE CARTRIDGE CARRIER

RELATED APPLICATIONS

This application claims the benefit of U.S. Provisional Patent Application Ser. Nos. 62/132,589, filed Mar. 13, 2015, and 62/132,618, filed Mar. 13, 2015, the entirety of each of which is hereby incorporated by reference for all purposes.

TECHNICAL FIELD

The present disclosure relates to devices and methods for sterile fluid production and, more particularly, to a multiple-bore solute cartridge carrier for use in a sterile fluid delivery system.

BACKGROUND

The use of portable fluid delivery systems in the medical field is known. A fluid delivery system may be used to dispense purified water, sterilized water, a sodium chloride solution, or any other fluid that may be needed during a medical procedure (e.g., surgery). Conventional portable fluid delivery systems rely on one or more containers (generally bags) for the supply of sterile fluid. The storage and transport of the bags, however, can be cumbersome. Additionally, certain medical procedures often require a greater volume of sterile fluid than what can be provided via the bags.

SUMMARY

The present disclosure relates to devices and methods for sterile fluid production and, more particularly, to a multiple-bore solute cartridge carrier for use in a sterile fluid delivery system.

In accordance with one aspect of the present disclosure, a multiple-bore solute cartridge carrier for use in a sterile fluid delivery system comprises a rotary housing adapted for connection to the sterile fluid delivery system. The rotary housing has one or more bores configured to receive a solute cartridge. The rotary housing, when connected to the sterile fluid delivery system, is selectively rotatable to facilitate creation of a desired sterile solution when sterile water from the fluid delivery system is flowed through the solute cartridge.

In accordance with another aspect of the present disclosure, a multiple-bore solute cartridge carrier for use in a sterile fluid delivery system comprises a rotary housing adapted for connection to the sterile fluid delivery system. The rotary housing has one or more bores configured to receive a solute cartridge. The rotary housing, when connected to the sterile fluid delivery system, is selectively rotatable to facilitate creation of a desired sterile solution when sterile water from the fluid delivery system is flowed through the solute cartridge. The rotary housing includes a central axis and the one or more bores are disposed circumferentially about the central axis.

In accordance with another aspect of the present disclosure, a multiple-bore solute cartridge carrier for use in a sterile fluid delivery system comprises a rotary housing adapted for connection to the sterile fluid delivery system. The rotary housing has one or more bores configured to receive a solute cartridge. The rotary housing, when connected to the sterile fluid delivery system, is selectively rotatable to facilitate creation of a desired sterile solution when sterile water from the fluid delivery system is flowed through the solute cartridge. The rotary housing includes a central axis and the one or more bores are disposed circumferentially about the central axis. The solute cartridge includes a frame, a filter supported by the frame, and a solute contained therein. The solute cartridge is formed separately, and removable from, a respective one of the bores.

BRIEF DESCRIPTION OF THE DRAWINGS

The foregoing and other features and advantages of the present disclosure will become apparent to those skilled in the art to which the present disclosure relates upon reading the following description with reference to the accompanying drawings, in which.

DETAILED DESCRIPTION

Definitions

Figure 1:
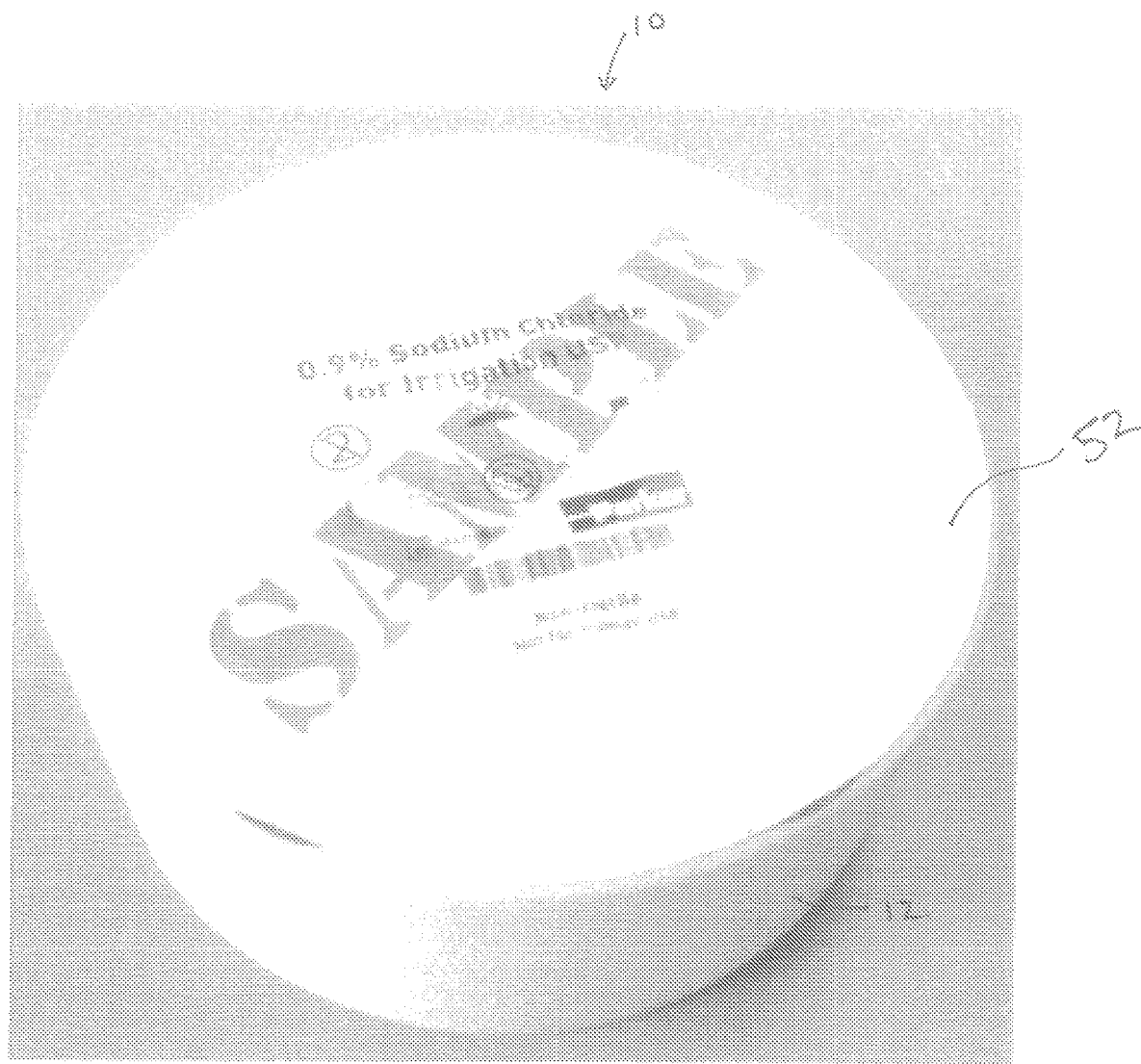
FIG. 1 is an image of a multiple-bore solute cartridge carrier, adapted for single-use with a sterile fluid delivery system, constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present.

In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

The present disclosure relates to devices and methods for sterile fluid production and, more particularly, to a multiple-bore solute cartridge carrier for use in a sterile fluid delivery system. The multiple-bore solute cartridge carrier 10 (FIG. 1) of the present disclosure, along with a sterile fluid delivery system (FIGS. 2-3), advantageously provides a stable and convenient way of storing a solute and dispensing a sterile fluid solution. The multiple-bore solute cartridge carrier 10 (FIG. 1) can easily and quickly be replaced to replenish the supply of solute, thereby overcoming drawbacks associated with conventional portable fluid delivery systems, such as fluid supply limitations, transportation and storage of fluid bags, etc. Additionally, the ease and quickness with which the multiple-bore solute cartridge carrier 10 can be replaced and/or swapped allows a user to readily change between different desired solutes.

Sterile Fluid Delivery System

The sterile fluid delivery system 70 provides on-demand delivery of a sterile fluid and/or solution. The sterile fluid delivery system 70 may be configured for a variety of uses such as, medical and/or household applications. The sterile fluid delivery system 70 can comprise a housing 84 configured to enclose components of the sterile fluid delivery system 70 including, but not limited to, a fluid conduit (not shown), a purification and/or sterilization mechanism (not shown), and a controller 86. The housing 84 may be made from a metal, metal alloy, plastic (e.g. polyethylene terephthalate, high density polyethylene, polyvinyl chloride), or a combination thereof. The housing 84 may be provided with a plurality of wheels 88 to assist with transportation of the sterile fluid delivery system 70.

The fluid conduit may be configured to convey fluid from an external fluid source (not shown) (e.g., a wall outlet port) to the purification and/or sterilization mechanism. One end of the fluid conduit may be adapted to mate with the external fluid source (e.g. a wall outlet port). Alternatively, the sterile fluid delivery system 70 may be free from attachment with an external fluid source and, instead, the fluid conduit may be adapted to mate with an internal fluid source. The internal fluid source (not shown) advantageously allows the sterile fluid delivery system 70 to be moved to any desired location without being constrained to a location near an external fluid source. The purification and/or sterilization mechanism may be, in one example, a filter of the type commercially available from Parker Hannifin Corp. (Cleveland, Ohio) (e.g. Fluflo Honeycomb Filter Cartridge, Part No. M19R10A-RS).

The controller 86 may be configured to command one or more operations of the sterile fluid delivery system 70 such as, fluid flow, fluid temperature, solution concentration etc. The controller 86 is in electrical communication with one or more components of the sterile fluid delivery system 70. The controller 86 may include various electrical components (e.g. microprocessor, memory, power source, etc.) The controller 86 may also include various software programs configured to control the sterile fluid delivery system 70. The software programs may comprise, for example, physician-specific or procedure-specific profiles that include personalize-able or pre-set control settings. The controller 86 may be located on a top portion of the housing 84, or at any other suitable location. The controller 86 is in electrical communication with one or more components of the sterile fluid delivery system 70.

In one example, the sterile fluid delivery system 70 is constructed as disclosed in U.S. Provisional Patent Application Ser. No. 62/132,618, filed Mar. 13, 2015, the entirety of which is hereby incorporated by reference.

Multiple-Bore Solute Cartridge Carrier

Figure 2:
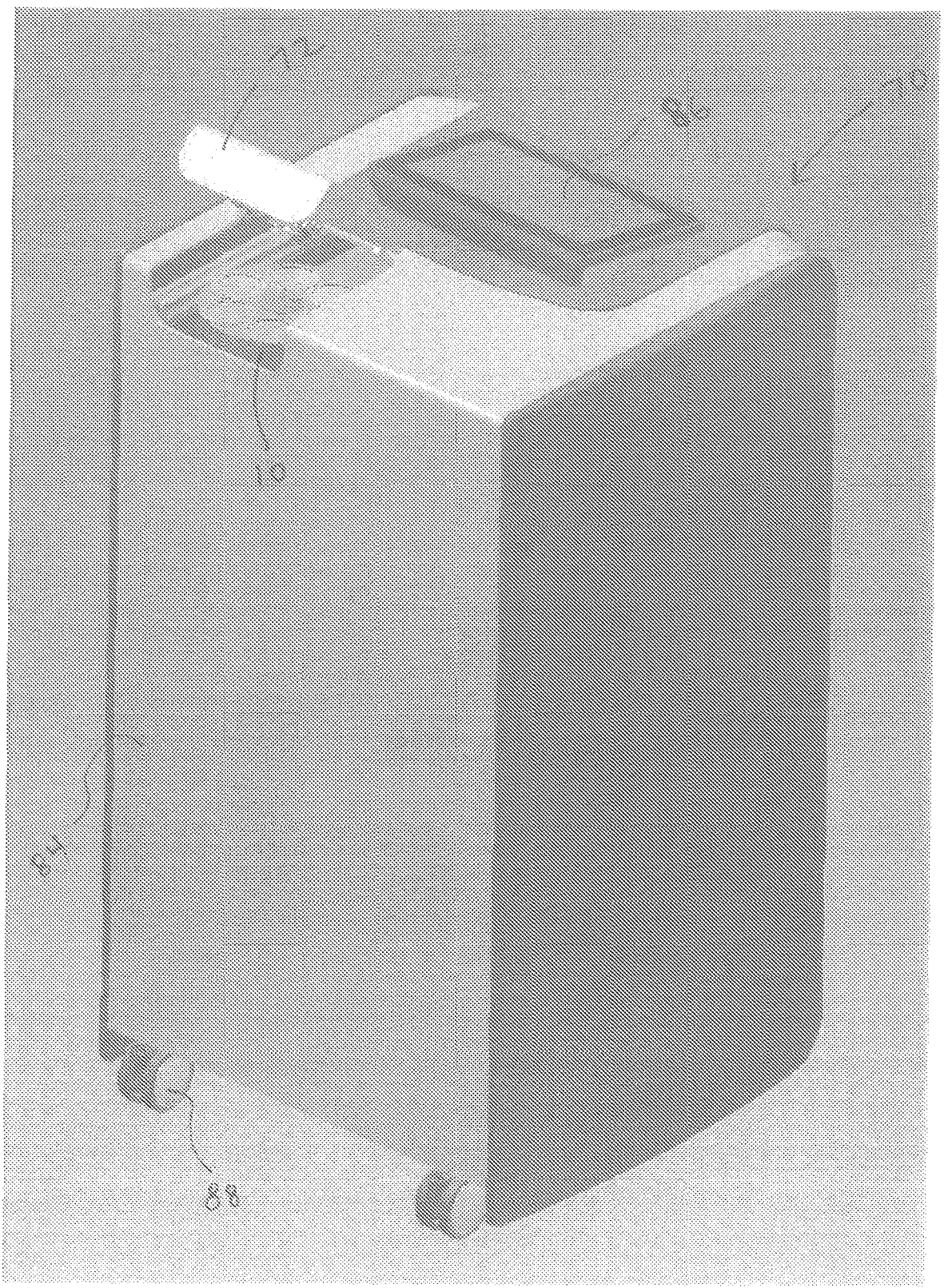
FIG. 2 is a perspective view showing a sterile fluid delivery system adapted for use with the multiple-bore solute cartridge carrier in FIG. 1.
Figure 3:
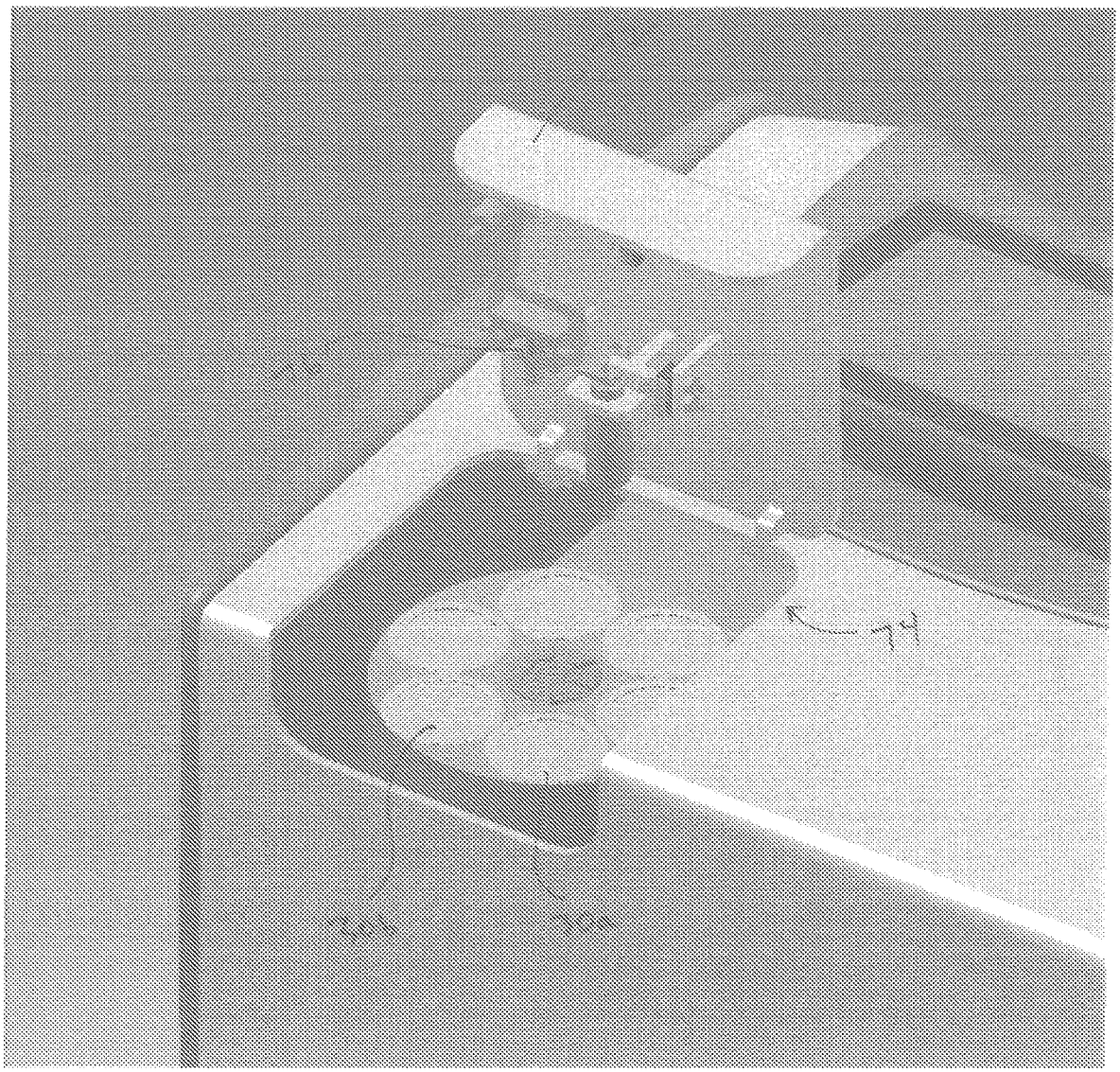
FIG. 3 is a partial detail view showing the sterile fluid delivery system in FIG. 2.

One aspect of the present disclosure includes a multiple-bore solute cartridge carrier 10 (FIG. 1) comprising a rotary housing 12 adapted for use with a sterile fluid delivery system 70 (FIGS. 2-3). The rotary housing 12 can be substantially O-shaped; however, other shapes are possible. The rotary housing 12 may be made of a metal, metal alloy, a plastic (e.g., polyethylene terephthalate, high density polyethylene, polyvinyl chloride), or a combination thereof.

Figure 4:
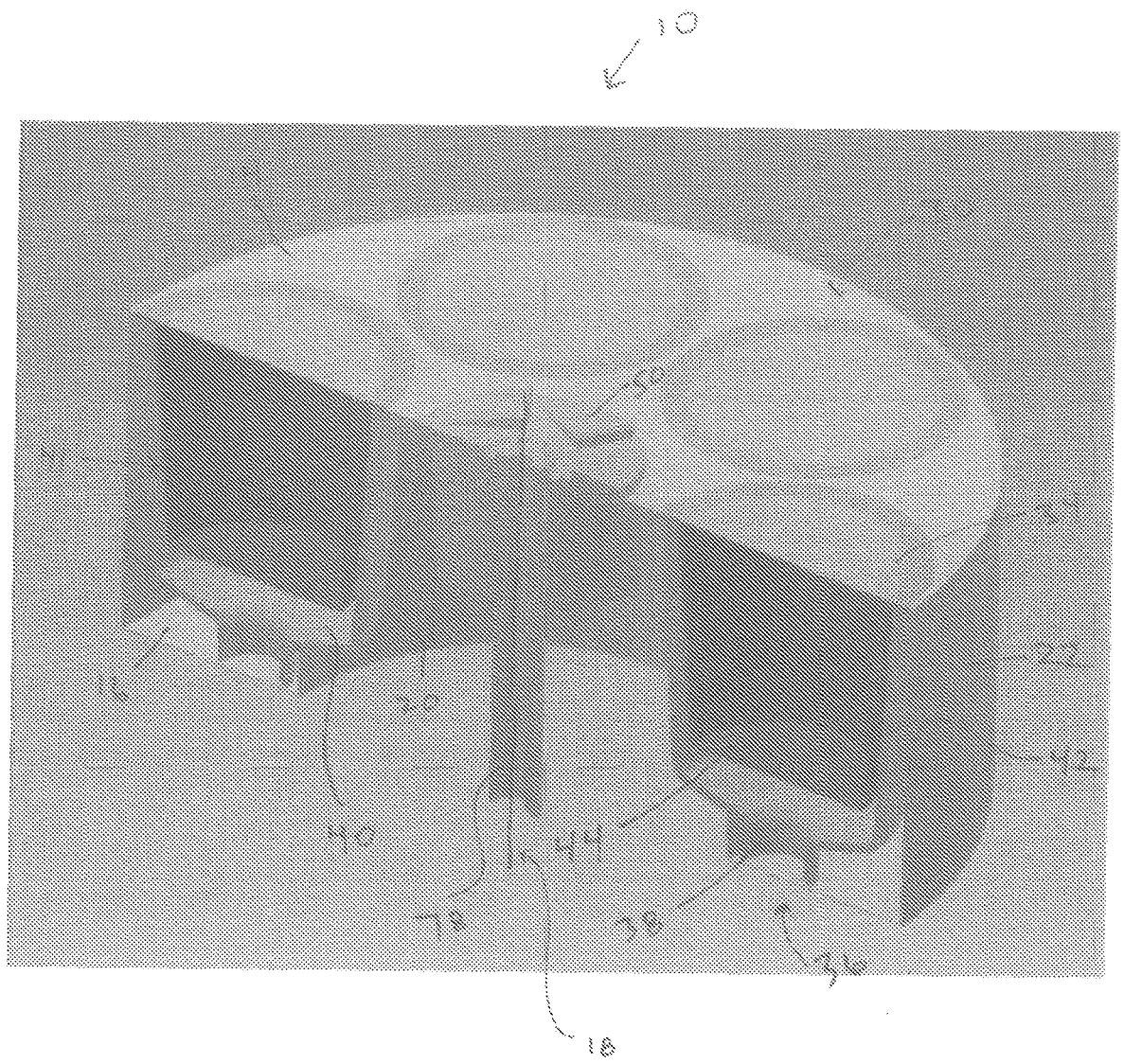
FIG. 4 is a perspective cutaway view of the multiple-bore solute cartridge carrier shown in FIG. 1.

Referring to FIG. 4, the rotary housing 12 is defined by an inner wall 20, an outer wall 22, oppositely disposed first and second surfaces 14, 16, and a central axis 18. The first surface 14 of the rotary housing 12 can include one or more rotary transmission elements 50. The rotary transmission elements 50 can be disposed equidistant from one another, and circumferentially about, the central axis 18 of the rotary housing 12. The rotary transmission elements 50 are configured to transmit rotary motion from the sterile fluid delivery system 70 to the cartridge carrier 10 to enable rotation of the cartridge carrier 10 relative to the sterile fluid delivery system 70.

Figure 5:
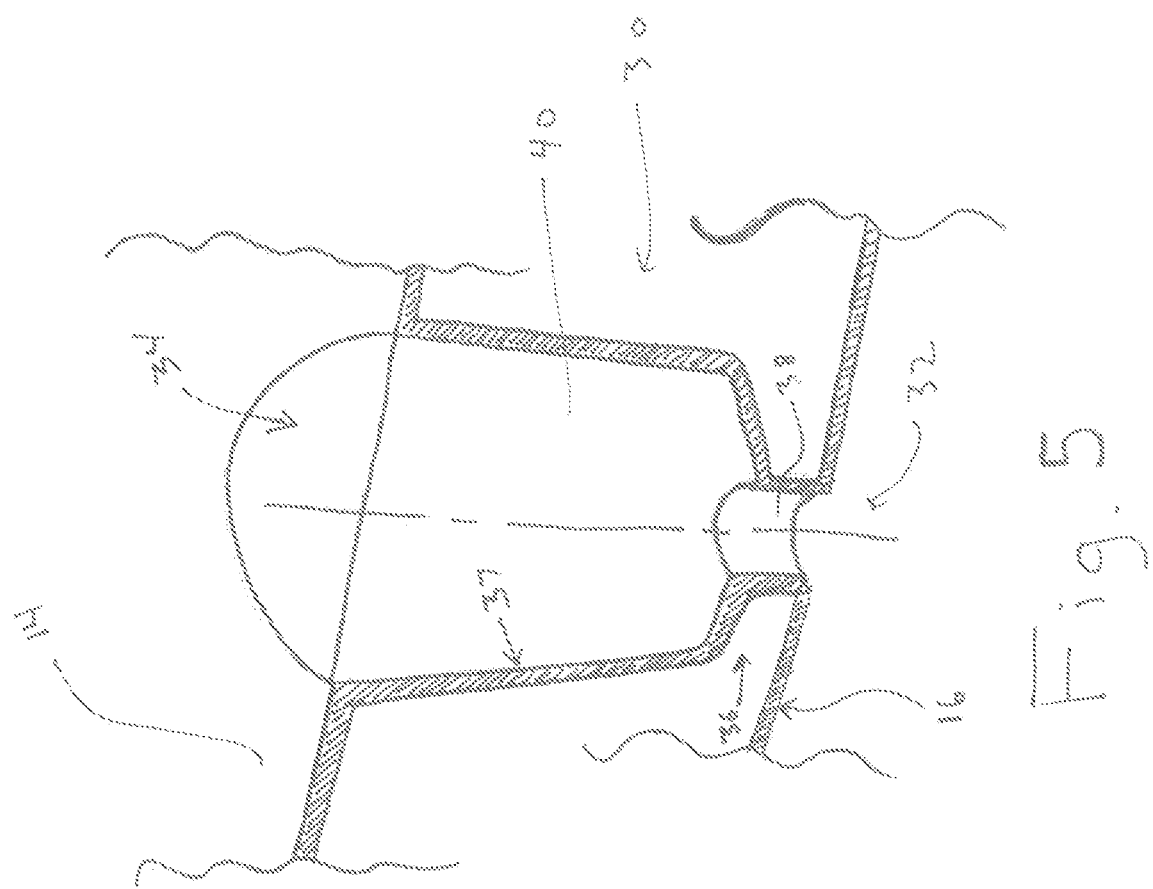
FIG. 5 is a perspective cutaway view of a single bore comprising the multiple-bore solute cartridge carrier in FIG. 1.

The rotary housing 12 can include one or more bores 30 extending between the first and second surfaces 14, 16. The bores 30 can be equally spaced apart from one another and disposed circumferentially about the central axis 18. In one example, the rotary housing 12 can include six bores 30. Each bore 30 (FIG. 5) extends along a central axis 32 between a filling end 34 and a draining end 36. The central axis 32 of each bore 30 extends substantially parallel to the central axis 18 of the rotary housing 12. Each bore 30 is at least partly defined by a substantially cylindrical inner wall surface 37. The filling end 34 is defined by a substantially circular opening in the first surface 14 of the rotary housing 12. A drain port 38 is located at the draining end 36. The drain port 38 extends coaxially with the central axis 32 through the second surface 16 of the rotary housing 12 so that the drain port 38, an interior volume 40 of the bore 30, and the filling end 34 are in fluid communication with one another.

Figure 6:
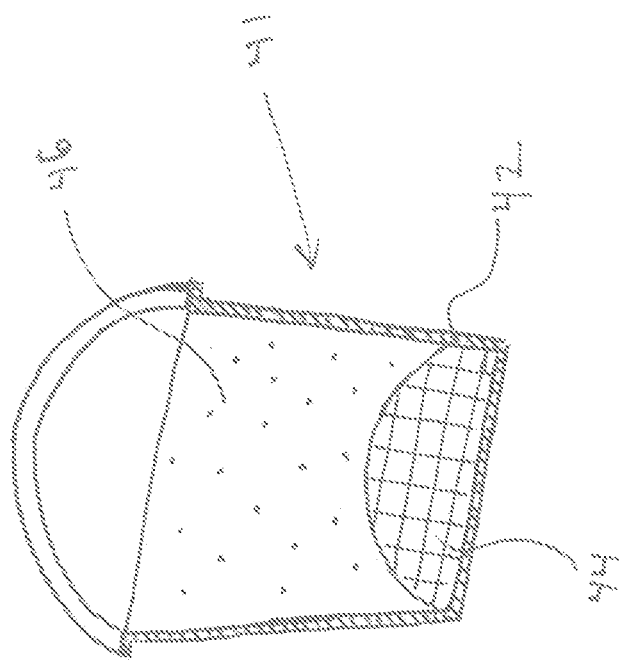
FIG. 6 is a perspective cutaway view of a single solute cartridge for use with the multiple-bore solute cartridge carrier in FIG. 1.

Each bore 30 is configured to receive a solute cartridge 41 (FIG. 6), which is removable from a respective bore 30. Each solute cartridge 41 is formed separately from a respective bore; however, in some instances, a solute cartridge 42 may be integrally formed with the inner wall surface 37 of a respective bore 30 such that the solute cartridge 42 is non-removable. Each solute cartridge 41 includes a frame 42 that supports a filter 44. The dimensions of the frame 42 are equal to (or substantially equal to) the interior dimensions of a bore 30. The frame 42 can be made of a metal, metal alloy, a plastic (e.g., polyethylene terephthalate, high density polyethylene, polyvinyl chloride), or a combination thereof.

The filter 44 is disposed at the bottom of the frame 42 and is located at the draining end 36 of the bore 30 when the solute cartridge 41 is positioned within the bore. The filter 44 can comprise a wire mesh that includes a plurality of openings, each of which have a diameter between about ten and one hundred microns, such as less than fifty microns (e.g., less than thirty microns). Each solute cartridge 41 is configured to hold or contain a solute 46, such as sodium chloride. Examples of other solutes that may be contained within a solute cartridge 41 can include lactate, potassium, calcium, dextrose, etc. Additionally, the solute cartridge 41 can be configured to hold or contain a pharmaceutical agent, such as antibiotics, antimicrobial agents, silver ions, etc.

A sealing material 52 closes and seals the filling end 34 of each bore 30, thereby closing off the interior volume 40 of each bore 30 from the exterior environment. In the configuration illustrated in FIG. 1, a single sheet of sealing material 52 is provided to seal all of the bores 30. The single sheet of sealing material 52 extends across the entire first surface 14 of the rotary housing 12. However, it will be appreciated that each bore 30 may be provided with a separate sheet of sealing material 52. In the configuration of FIG. 1, for example, six separate sheets of sealing material 52 would be provided so that each individual bore 30 is sealed with a separate one of the six sheets. In some instances, the sealing material 52 is made of a metal foil that can be punctured during operation of the sterile fluid delivery system 70. It is contemplated that any other material(s) can be used to form the sealing material 52. For example, the sealing material 52 can be made of a rubber membrane having a number of self-sealing slits through which certain components of the sterile fluid delivery system 70 can selectively extend.

In one aspect, the multiple-bore solute cartridge carrier 10 can include one or more radio frequency identification (RFID) tags associated with one or more of the solute cartridges 41. The RFID tag(s) can communicate with the controller 86 of the sterile fluid delivery system 70 to indicate the solute contents of each solute cartridge 41. The contents of the solute cartridges 41 can also be determined by having the sterile fluid delivery system 70 sense a physical characteristic of the solute cartridges 41, such as color, weight, and/or size, etc. Additionally, or optionally, the RFID tag(s) can provide information relating to ideal operating parameters (e.g., temperature, flow rate, etc.) of the sterile fluid delivery system 70 to optimize production of the solution.

Figure 7:
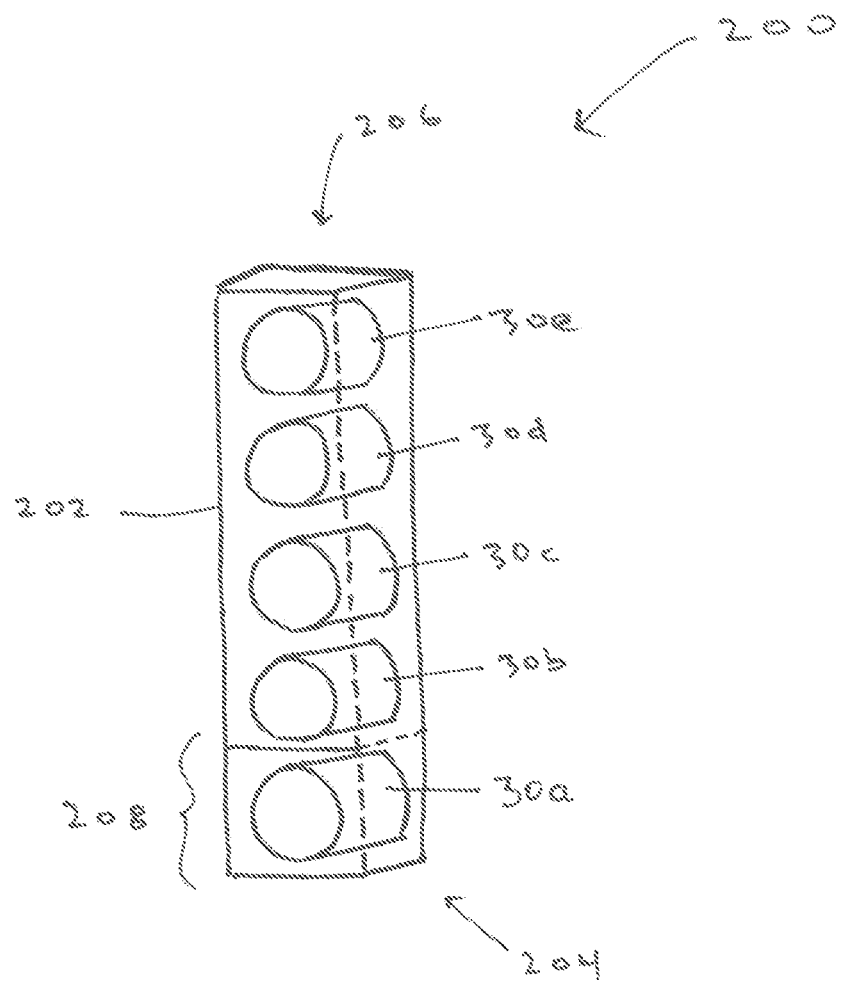
FIG. 7 is a perspective view of a solute cartridge carrier constructed in accordance with another aspect of the present disclosure.

In another aspect, a solute cartridge carrier 200 (FIG. 7) can be configured as a substantially cuboid housing 202. The housing 202 can define an interior space configured to receive a plurality of cartridges 30a-30e of the type shown in FIG. 6. The carrier 200 can have a first end 204, a second end 206, and an operating section 208 at the first end. The operating section 208 can include a disposal door (not shown).

In use, the cartridges 30 can be loaded into the carrier 200 at the second end 206. The sterile fluid delivery system 70 can interact with the cartridge 30a positioned in the operation section 208 to produce a desired solution. When the supply of solute in the first cartridge 30a is exhausted, the sterile fluid delivery system 70 can open the disposal door to eject the exhausted cartridge from the first end 204 and advance the second cartridge 30b into the operation section 208.

Method of Use

Use of a multiple-bore solute cartridge carrier 10 (FIGS. 2-3) in a sterile fluid delivery system 70 to produce a sterile fluid solution will now be described. First, a door 72 provided on the sterile fluid delivery system 70 is opened to reveal a cartridge retaining area 74. The door 72 may have locking features that prevent unauthorized access to the cartridge retaining area 74. The cartridge retaining area 74 can include a fluid nozzle 76, a drain nozzle (not shown), and a rotary transmission member 78 (FIG. 4). The cartridge carrier 10 is placed in the cartridge retaining area 74 such that the rotary transmission member 78 engages the rotary transmission receiving depressions 50, thereby rotatably fixing the cartridge carrier 10 to the rotary transmission member 78. Next, the door 72 is closed.

The sterile fluid delivery system 70 includes a drive mechanism (not shown) that rotates the rotary transmission member 78 and causes likewise rotation of the cartridge carrier 10 about the central axis 18 of the rotary housing 12. The cartridge carrier 10 is rotated until the drain nozzle in the cartridge retaining area 74 is aligned with the drain port 38 of a first bore 30a. Aligning the drain nozzle with the drain port 38 also substantially aligns the fluid nozzle 76 with the central axis 32 of the first bore 30a. The system 70 then drives the fluid nozzle 76 to pierce the sealing material 52 covering the filling end 34 of the first bore 30a. The fluid nozzle 76 is thereby positioned in the interior volume 40 of the first bore 30a so that the fluid nozzle is in fluid communication with the solute cartridge 48. As the fluid nozzle 76 pierces the sealing material 52, the drain nozzle is simultaneously moved into fluid communication with the drain port 38.

Next, the sterile fluid delivery system supplies 70 sterile fluid (e.g. water) to the fluid nozzle 76. The sterile fluid delivery system 70 may modulate certain properties of the sterile fluid before it is supplied to the fluid nozzle 76, such as temperature, conductivity, pathogen count, etc. The sterile fluid flows from the fluid nozzle 76 into the solute cartridge 41 to dissolve the solute 46 (e.g., sodium chloride) to create a sterile sodium chloride solution. The sterile sodium chloride solution passes through the filter 44 and out of the bore 30a via the drain port 38. The sterile sodium chloride solution flows from the drain port 38 and is received by the drain nozzle. The drain nozzle is fluidly coupled to additional components of the sterile fluid delivery system 70, which enable on-demand delivery of the sterile sodium chloride solution.

Eventually, the supply of sodium chloride in the solute cartridge 41 will be exhausted, at which point it is necessary to index the cartridge carrier 10 from the first bore 30a to a second bore 30b if additional sterile sodium chloride solution is desired. The level of sodium chloride contained within each solute cartridge 48 may be ascertained, for example, by monitoring the resulting sterile sodium chloride solution to determine when the solution concentration drops below a desired concentration. Alternatively, the sterile fluid delivery system 70 may be provided with information relating to the amount of solution that can be produced by each solute cartridge 48. For example, the sterile fluid delivery system 70 may be programmed to recognize that the supply of sodium chloride solute 46 in one solute cartridge 41 will be exhausted once a certain volume of sterile sodium chloride solution has been created.

When it is desirable to index the cartridge carrier 10 from the first bore 30a to the second bore 30b, the sterile fluid delivery system 70 ensures that the supply of sterile water to the fluid nozzle 76 is stopped. For example, the cartridge carrier 10 can include a detection mechanism (not shown) for communicating with the controller 86 to signal the indexed position of the cartridge carrier. Additionally, or alternatively, the detection mechanism can signal when the cartridge carrier 10 needs to be replaced.

Next, the sterile fluid delivery system 70 simultaneously withdraws the fluid nozzle 76 from the interior volume 40 of the first bore 30a and the drain nozzle out of fluid engagement with the drain port 38. The sterile fluid delivery system 70 then actuates the rotary transmission member 78 to rotate the cartridge carrier 10 until the central axis 32 of the second bore 30b is in alignment with the fluid nozzle 76. At this point, the above-described process can be repeated to prepare additional sterile fluid solution (e.g., sterile sodium chloride solution).

From the above description of the present disclosure, those skilled in the art will perceive improvements, changes and modifications. For example, the sterile fluid delivery system 70 can be configured to hold the multiple-bore solute cartridge carrier 10 stationary and move the drain nozzle and drain port 38 relative to the multiple-bore solute cartridge carrier 10 to index between the bores 30. As a further example, the sterile fluid delivery system 70 can include a plurality of drain nozzles and drain ports 38 that are configured to simultaneously engage a plurality of the bores 30 to allow for the concurrent production of different solutions that can be combined in the sterile fluid delivery system 70 and delivered on-demand to a desired site. Such improvements, changes, and modifications are within the skill of the art and are intended to be covered by the appended claims. All patents and patent applications identified herein are hereby incorporated by reference for all purposes.

The following is claimed:

1. A multiple-bore solute cartridge carrier for use in a sterile fluid delivery system, the carrier comprising:
   a rotary housing adapted for connection to the sterile fluid delivery system, the rotary housing having oppositely disposed first and second surfaces, the rotary housing including one or more bores extending between the first and second surfaces, each bore extending along a central axis between a filling end and a draining end, each bore being at least partially defined by an inner wall surface, each inner wall surface defining a cartridge receiving portion and a drain port of an associated bore, each drain port extending through the second surface of the rotary housing and away from the second surface of the rotary housing to the cartridge receiving portion of an associated bore; and
   one or more solute cartridges received in the cartridge receiving portion of the one or more bores, each solute cartridge including a frame, a filter supported by the frame, and a solute contained therein, each filter substantially extending perpendicular with respect to an associated central axis so that water, when flowing from the filling end to the draining end of an associated bore, flows through the filter;
   wherein the sterile fluid delivery system is configured to flow water through the one or more solute cartridges to create a desired sterile solution.

2. The multiple-bore solute cartridge carrier according to claim 1, wherein the rotary housing, when connected to the sterile fluid delivery system, is selectively rotatable to facilitate creation of the desired sterile solution.

3. The multiple-bore solute cartridge carrier according to claim 1, wherein the solute is a pharmaceutical agent.

4. The multiple-bore solute cartridge carrier according to claim 3, wherein the pharmaceutical agent is at least one of an antibiotic, an antimicrobial agent, and silver ions.

5. The multiple-bore solute cartridge carrier according to claim 1, wherein the rotary housing includes a central axis and the one or more bores are disposed circumferentially about the central axis.

6. The multiple-bore solute cartridge carrier according to claim 1, wherein the solute is one of a combination of sodium, chloride, lactate, potassium, calcium, and dextrose.

7. The multiple-bore solute cartridge carrier according to claim 1, wherein the frame of each of the one or more solute cartridges is integrally formed with an inner surface defining a respective bore.

8. The multiple-bore solute cartridge carrier according to claim 1, wherein the solute cartridge is formed separately, and removable from, a respective one of the bores.

9. The multiple-bore solute cartridge carrier according to claim 1, wherein an end of the solute cartridge is sealed by a sealing material.

10. The multiple-bore solute cartridge carrier according to claim 1, wherein prior to being received in the sterile fluid delivery system, the entire rotary housing is covered by a sealing material so that the multiple-bore solute cartridge carrier is adapted for single-use operation with the sterile fluid delivery system, the sealing material closing and sealing the filling end of the one or more bores thereby closing off an interior volume of the one or more bores from an exterior environment.

11. The multiple-bore solute cartridge carrier according to claim 1, wherein the filter is designed to filter solids between ten and one hundred microns.

12. The multiple-bore solute cartridge carrier according to claim 1, wherein each drain port has a smaller diameter than an associated cartridge receiving portion.

13. A system for on-demand delivery of a sterile fluid, comprising:
   a housing;
   at least one fluid reservoir that is associated with the housing and configured to hold a fluid;
   a sterilization and/or purification mechanism in fluid communication with the at least one fluid reservoir, the sterilization and/or purification mechanism being configured to sterilize the fluid;
   a solution production mechanism in fluid communication with the sterilization and/or purification mechanism, the solution production mechanism being configured to receive the sterile fluid from the sterilization and/or purification mechanism, the solution production mechanism including a multi-bore solute cartridge carrier received in the housing, the multi-bore solute cartridge carrier including:
      a rotary housing having oppositely disposed first and second surfaces, the rotary housing having one or more bores extending between the first and second surfaces, each bore extending along a central axis between a filling end and a draining end, each bore being at least partially defined by an inner wall surface, each inner wall surface defining a cartridge receiving portion and a drain port of an associated bore, each drain port extending through the second surface of the rotary housing and away from the second surface of the rotary housing to the cartridge receiving portion of an associated bore, and one or more solute cartridges received in the cartridge receiving portion of the one or more bores, each solute cartridge including a frame, a filter supported by the frame, and a solute contained therein, each filter substantially extending perpendicular with respect to an associated central axis so that the sterile fluid, when flowing from the filling end to the draining end of an associated bore, flows through the filter, the solution production mechanism being configured to selectively flow the received sterile fluid through the one or more solute cartridges to mix the received sterile fluid with the solute to produce a sterile solution;

a dispensing mechanism that is in fluid communication with the sterilization and/or purification mechanism, the dispensing mechanism being configured to dispense one or more of the sterile fluid and the sterile solution; and a controller associated with one or more of the housing, the at least one fluid reservoir, the sterilization and/or purification mechanism, the solution production mechanism, and the dispensing mechanism, the controller being configured to modulate at least one operating characteristic of the system;

wherein the system is configured to deliver one or more of the sterile fluid and the sterile solution immediately after the request is made.

14. The multiple-bore solute cartridge carrier according to claim 1, wherein each filter substantially extends perpendicular with respect to a direction in which water exits through a drain port of an associated bore.

* * * * *